United States Patent [19]

Clarke et al.

[11] Patent Number: 5,264,368

[45] Date of Patent: Nov. 23, 1993

[54] HYDROCARBON LEAK SENSOR

[75] Inventors: Richard H. Clarke, Scituate; T. Eric Hopkins, Wellesley; Wai Chung, Watertown; Stephen DeJesus, Newton; Harvey Harrison, Needham, all of Mass.

[73] Assignee: Boston Advanced Technologies, Inc., Newton, Mass.

[21] Appl. No.: 822,097

[22] Filed: Jan. 17, 1992

Related U.S. Application Data

[63] Continuation-in-part of Ser. No. 769,948, Sep. 30, 1991, abandoned, and a continuation-in-part of Ser. No. 595,037, Oct. 10, 1990, abandoned.

[51] Int. Cl.$^5$ .................. G01N 21/64; G08B 21/00
[52] U.S. Cl. .......................... 436/3; 73/49.2; 73/61.48; 73/61.61; 250/301; 340/605; 340/623; 340/624; 422/68.1; 422/82.05; 422/82.08; 422/82.09; 436/27; 436/56; 436/60; 436/134; 436/172
[58] Field of Search .............. 73/49.1, 49.2, 61.61, 73/61.48; 200/61.04, 84 B, 84 C; 250/301, 302; 307/118; 340/605, 623, 624; 422/68.1, 82.05, 82.08, 82.09; 436/3, 27, 56, 60, 139, 172

[56] References Cited

U.S. PATENT DOCUMENTS

| | | | |
|---|---|---|---|
| 2,593,391 | 4/1952 | Bray | 250/53 |
| 3,061,723 | 10/1962 | Kapff | 250/71 |
| 3,200,645 | 8/1965 | Levins | 200/84 C |
| 3,428,074 | 2/1969 | Perren | 200/61.04 |
| 3,681,028 | 8/1972 | Mason | 436/139 X |
| 3,697,256 | 10/1972 | Hirschfeld et al. | 23/254 |
| 3,719,936 | 3/1973 | Daniels et al. | 340/605 X |
| 3,725,658 | 4/1973 | Stanley et al. | 250/71 |
| 3,842,270 | 10/1974 | Gregory et al. | 250/301 |
| 4,058,802 | 11/1977 | Meyers | 340/605 X |
| 4,351,642 | 9/1982 | Bonavent et al. | 23/230 |
| 4,501,324 | 2/1985 | Sandiford et al. | 166/250 |
| 4,536,322 | 8/1985 | Amstutz et al. | 252/301 |
| 4,555,627 | 11/1985 | McRae, Jr. | 250/334 |
| 4,563,674 | 1/1986 | Kobayashi | 340/605 X |
| 4,586,033 | 4/1986 | Andrejasich | 340/605 X |
| 4,632,807 | 12/1986 | Marsoner | 422/68 |
| 4,643,877 | 2/1987 | Opitz et al. | 422/68 |
| 4,644,354 | 2/1987 | Kidd | 340/870 |
| 4,661,320 | 4/1987 | Ito et al. | 422/86 |
| 4,662,940 | 5/1987 | Monier | 106/33 |
| 4,677,078 | 6/1987 | Minten et al. | 436/136 |
| 4,709,577 | 12/1987 | Thompson | 73/40 |
| 4,721,950 | 1/1988 | Andrejasich | 340/605 X |
| 4,752,447 | 6/1988 | Kimmel et al. | 422/56 |
| 4,754,136 | 6/1988 | Blakely | 250/301 |
| 4,755,469 | 7/1988 | Showalter et al. | 436/27 |
| 4,758,366 | 7/1988 | Parekh | 252/68 |
| 4,762,420 | 8/1988 | Bowley | 356/436 |
| 4,770,028 | 9/1988 | Flippo, Jr. | 73/40 |
| 4,771,006 | 9/1988 | Miller et al. | 436/126 |
| 4,773,422 | 9/1988 | Isaacson et al. | 128/633 |
| 4,782,234 | 11/1988 | Caudyk et al. | 250/372 |
| 4,802,761 | 2/1989 | Bowen et al. | 356/301 |
| 4,818,976 | 4/1989 | Schmitt et al. | 340/605 |
| 4,863,694 | 9/1989 | Kimmel et al. | 422/86 |
| 4,892,383 | 1/1990 | Klainer et al. | 350/96 |
| 4,897,551 | 1/1990 | Gersh et al. | 250/461 |
| 4,899,047 | 2/1990 | Cary et al. | 250/227 |
| 4,912,051 | 3/1990 | Zaromb | 436/178 |
| 5,079,944 | 1/1992 | Boenning et al. | 73/31.05 X |

FOREIGN PATENT DOCUMENTS 58-166237 10/1983 Japan .
60-213842 10/1985 Japan .

*Primary Examiner*—James C. Housel
*Assistant Examiner*—Arlen Soderquist
*Attorney, Agent, or Firm*—Thomas J. Engellenner

[57] ABSTRACT

Method and apparatus for detecting and/or monitoring the presence of hydrocarbons in a fluid medium at a remote location, by sensing the presence of hydrocarbon-based fluid in the fluid medium in the remote location, generating a signal indicative of the sensed fluid, and transmitting the signal to monitoring means for indication of hydrocarbon contamination. The apparatus has multiple sensors at different vertical levels for sensing the fluid medium at a plurality of levels within the fluid.

28 Claims, 3 Drawing Sheets

5,264,368

HYDROCARBON LEAK SENSOR

REFERENCE TO RELATED APPLICATION

This application is a continuation-in-part of U.S. application Serial No 07/769,948, filed Sep. 30, 1991, and a continuation-in-part of U.S. application Ser. No. 07/595,037, filed Oct. 10, 1990 both now abandoned.

BACKGROUND OF THE INVENTION

The present invention relates to fluid leak detection, and more particularly, to a hydrocarbon leak sensor for detection of fluid leakage from hydrocarbon fluid storage containers.

The detection and measurement of groundwater contaminants is of considerable interest. It is of particular interest to monitor the integrity of tanks containing potential environmental pollutants. For example, gasoline and oil tanks can cause severe contamination of the local environment, if such tanks leak.

Since it is usually impractical to conduct a manual or visual inspection of a buried storage tank, various remote sensing systems have been devised. For example, bore holes can be drilled and groundwater samples can be taken for off-site chemical analysis. However, sampling is time-consuming and expensive. Moreover, because physical sampling is only a periodic action, it is unlikely to be able to detect a leak or spill promptly and before significant damaged has occurred.

Various instruments for continuous monitoring of groundwater and the like have also been proposed, based on measurements, for example, of changes in dielectric properties or infrared spectral analysis of the contaminated fluids. However, these systems are typically very expensive and prone to maintenance problems.

It is therefore an object of the present invention to provide a sensor system capable of continuous monitoring for groundwater contamination.

It is another object of the present invention to provide an inexpensive, robust and compact sensor device which can be placed in a remote location, such as in a sump hole, in the drain pan under a fuel pump, or in the interstitial access between inner and outer walls of a double-walled storage tank, for detection of hydrocarbon fluid leakage.

Furthermore, it is preferable that in situ leakage sensor devices be inexpensive and be able to discriminate between groundwater and hydrocarbon fluids, and that the sensing be relatively unaffected by the amount of groundwater.

It is therefore another object of the present invention to provide an inexpensive and self-contained sensor device which can discriminate between groundwater and hydrocarbon fluid and can provide accurate measurements of hydrocarbon fluid at various levels of groundwater.

SUMMARY OF THE INVENTION

The present invention provides an improved method and apparatus for detecting and/or monitoring the presence of hydrocarbons in a fluid medium at a remote location, by sensing the presence of hydrocarbon-based fluid in the fluid medium in the remote location, generating a signal indicative of the sensed fluid, and transmitting the signal to monitoring means for indication of hydrocarbon contamination. The remote location may be a sump hole, or the drain pan under a fuel pump, or the interstitial access between inner and outer walls of a double-walled storage tank, or the like, where detection of hydrocarbon fluid leakage is desired.

In one embodiment, a sensor device is disclosed having a housing and at least one chamber which receives a sample of the fluid medium, and detects the presence of hydrocarbons therein by illuminating the sample and measuring the optical properties of the sample.

In one aspect of the invention, wireless communication means for wirelessly transmitting the sensor signals to the monitoring means is disclosed. Various wireless means including infrared radiation, radio waves or magnetic inductance, for example, can be employed to eliminate the need for hardwired connection of the sensor device to the monitoring means.

In another aspect of the invention, the sensor device is buoyant such that the sensor device can float on the fluid medium, and the sensor device measures the level of hydrocarbon fluid from the surface of the fluid medium. According to this aspect, means for adjusting the buoyancy of the sensor device may be provided to change the level at which the sensor detects hydrocarbons in the fluid medium.

In another aspect of the invention, the sensor device includes a plurality of fluid level sensor elements for measuring a plurality of layers of hydrocarbon fluid of varying thicknesses, relative to the surface of the fluid medium, when the sensor device is floating upon the fluid medium.

In still another aspect of the invention, means are provided for detecting hydrocarbon contamination of the fluid medium when the sensor device is not afloat.

BRIEF DESCRIPTION OF THE DRAWINGS

These and other features and advantages of the present invention will be more fully understood by reference to the following detailed description in conjunction with the attached drawing in which like reference numerals refer to like elements and in which.

DETAILED DESCRIPTION

Figure 1:
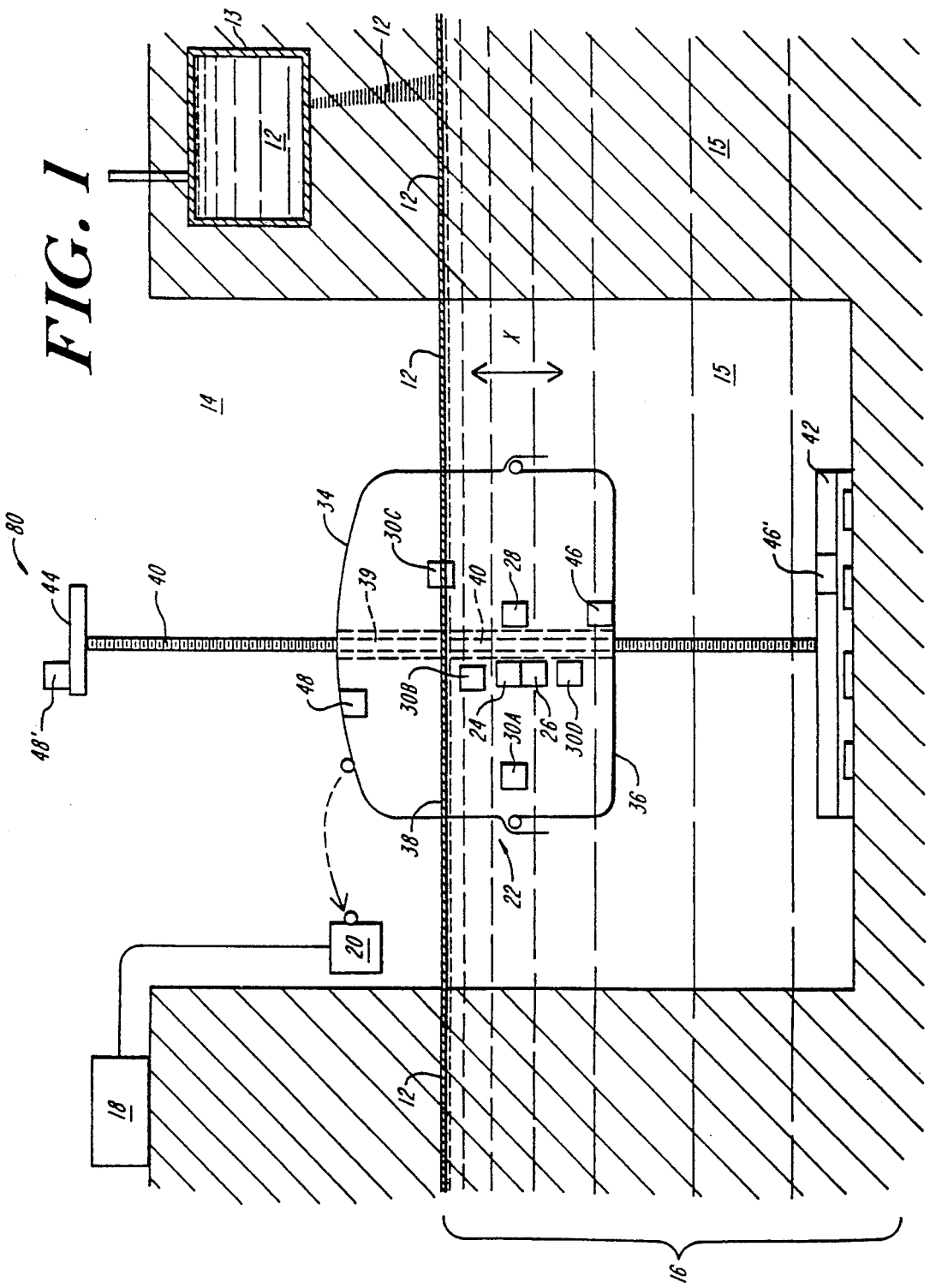
FIG. 1 is a schematic plan view of a sensor system of the invention.

A system for external monitoring of a hydrocarbon fluid storage tank according to the invention is shown in FIG. 1 in which a buoyant sensor device 10 detects the presence of hydrocarbon fluid 12 which has escaped from tank 13 into a bore hole 14. The bore hole gives access to local groundwater 15, which typically becomes contaminated with the hydrocarbon-based fluid losses from the tank.

The lost hydrocarbon fluid and groundwater collects as a fluid medium 16 within the bore hole, and buoyant sensor device 10 floats on this fluid medium. The sensor device generates an output signal indicative of the presence of hydrocarbon fluid 12 which it detects.

Fluid medium 16 is shown in bore hole 14 having a layer of hydrocarbon fluid 12 riding on groundwater 15. In practice of the invention, this hydrocarbon fluid layer 12 is discriminated from the supporting groundwater 15, and thus is separately detected by use of sensor device 10, as a means of detection of hydrocarbon leakage.

Sensor device 10 operates in conjunction with a contamination monitor-display-warning unit 18, which includes a receiver device 20. As further shown in the combination of FIGS. 1-3, the sensor device includes a housing 22, which contains a wireless transmitter 24, drive electronics package 26, and power supply 28 (such as a rechargeable battery), as well as sensor elements 30A-C. Electronics package 26 issues an output via transmitter 24 indicative of hydrocarbon fluid detections made by sensor elements 30A-C. The electronics package includes a timer device 29 for reducing power drain and increasing battery life, and therefore sensor device 10 may take readings and issue a report at preset intervals, rather than transmitting continuously. The device may also generate and emit a "low battery" signal. The hydrocarbon-fluid sensing elements 30A-C communicate with the periphery 32 of the sensor device and generate a respective sense signal indicative of sensed hydrocarbon fluid at the level to which the specific sensor element is assigned.

The present invention benefits from the recognition that the conventional hardwired connection of a sensor device to the monitor can cause inaccuracies in fluid level detection. Therefore the battery-operated sensor device 10 wirelessly transmits its output to a monitor unit located remotely from the sensor device for indication of the presence of hydrocarbon fluid.

The sensor device housing 22 extends along a floatation axis X, generally parallel with the walls of the bore hole. The housing has a nominal buoyancy such that the top 34 of housing 22 rides out of fluid medium 16, while the bottom 36 of the housing is submerged. Furthermore, since the sensor device 10 has a known buoyancy, a fluid draft line 38 (i.e., a calibration index) can be established at a known location, nominally perpendicular to floatation axis X. The sensor elements 30A-C therefore can be located along axis X at known stations (or windows) below and relative to the draft line. As a result, the three sensor elements can give three separate indications of greater and greater or lesser and lesser hydrocarbon fluid layer thickness, measured relative to the surface of the fluid medium 16 in which sensor device 10 is floating.

The sensor elements interact with the fluid medium via windows in the housing periphery 32. Hydrocarbon sensor element 30A is located at window W1 a distance "A" below draft line 38, with hydrocarbon sensor element 30B located at window W2 a distance "B" below the draft line, and with hydrocarbon sensor element 30C located at window W3 a distance "C" below the draft line. Therefore each such sensor element is assigned to detection of a respective one of several fluid levels of ever increasing thickness of hydrocarbon fluid measured down from the draft line. For example, if $A = \frac{1}{4}''$, $B = \frac{1}{8}''$, and $C = 1/16''$, then sensor element 30C detects a 1/16'' hydrocarbon fluid depth measured from the surface of the fluid medium 16, sensor element 30B detects a $\frac{1}{8}''$ hydrocarbon fluid depth measured from the surface of the fluid medium 16, and sensor element 30A detects a $\frac{1}{4}''$ hydrocarbon fluid depth measured from the surface of the fluid medium, when the sensor device is afloat and the draft line is at the surface of the fluid medium.

Nevertheless, a minimum draft for sensor device 10 is desirable to eliminate the "dead time" during which fluid medium 16 may be accumulating before the sensor device floats, i.e., when the sensor device is "bottomed out" and therefore is not capable of measuring the thickness of the hydrocarbon layer relative to the draft line. The materials out of which the invention is constructed are selected to reduce its weight and increase its buoyancy, so as to reduce this dead time.

Returning to FIG. 1, it will be appreciated that sensor device 10 is doughnut-like, having a central passage 39, and that the sensor device 10 is mounted via passage 39 on a guidance means, such as guide rail 40. The guide rail extends between a guide rail base 42 and guide rail cap 44 along axis X. The guide rail assures that the floating sensor is not interfered with by physical obstructions along the surface of the bore hole, and the base 42 lifts the sensor out of any mud accumulation at the bottom of the bore hole.

Sensor device 10 further includes a position sensor 46 which informs the user whether the sensor device is in a "bottomed out" or "floating" condition. In one embodiment, the position sensor 46 cooperates with a magnet 46' in rail base 42 for detection of the bottomed condition. As a result, when the sensor device is floating, sensor 46 is separated from magnet 46' and generates a "floating" indication, which is communicated via electronics package 26 and transmitter 24 to monitor 18 via receiver 20. Thus, when the "floating" indication is received, readings from elements 30A-C will be known to be relative to draft line 38, and will be interpreted accordingly.

In addition to the foregoing, the sensor apparatus may further include top position sensor 48 and cooperating magnet 48' mounted on rail cap 44 so that it will be known when the sensor device has "topped out" against the rail cap, and therefore is not capable of floating with the rising fluid medium.

In an alternative embodiment, a fourth hydrocarbon sensor element 30D is provided at window W4 $\frac{1}{8}''$ (D) above the bottom 36' of the sensor device bottom 36 and $\frac{1}{8}''$ (D') below the lowest sensor element 30A. This sensor element is useful when the sensor device 10 is bottomed on base 42. If hydrocarbon fluid is detected at element 30D, it will not be known whether this hydrocarbon fluid is a layer on a base of groundwater or is all hydrocarbon fluid, but as the fluid medium rises from element 30D to 30A, further information can be obtained depending upon whether the hydrocarbon layer spans one or both elements 30A and 30D.

Nevertheless the sensor device 10 is most useful when floating, since sensor element 30C can detect a first hydrocarbon layer 12 on the groundwater 15, sensor element 30B can detect a thicker layer and sensor element 30A can detect a yet thicker layer, relative to the fluid medium surface (i.e., from draft line 38).

Figure 2:
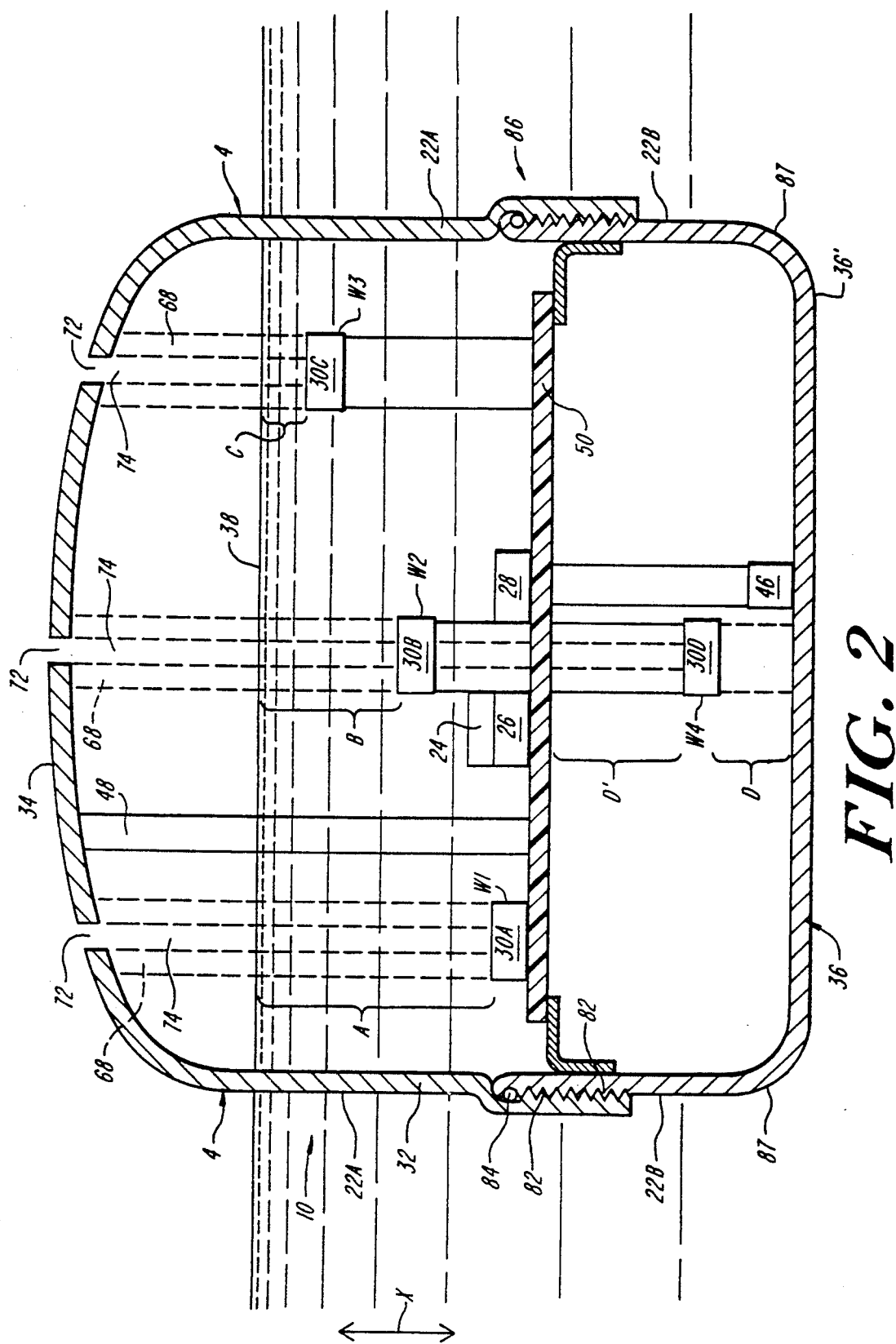
FIG. 2 is a more detailed, schematic, side view of the sensor device of FIG. 1.
Figure 3:
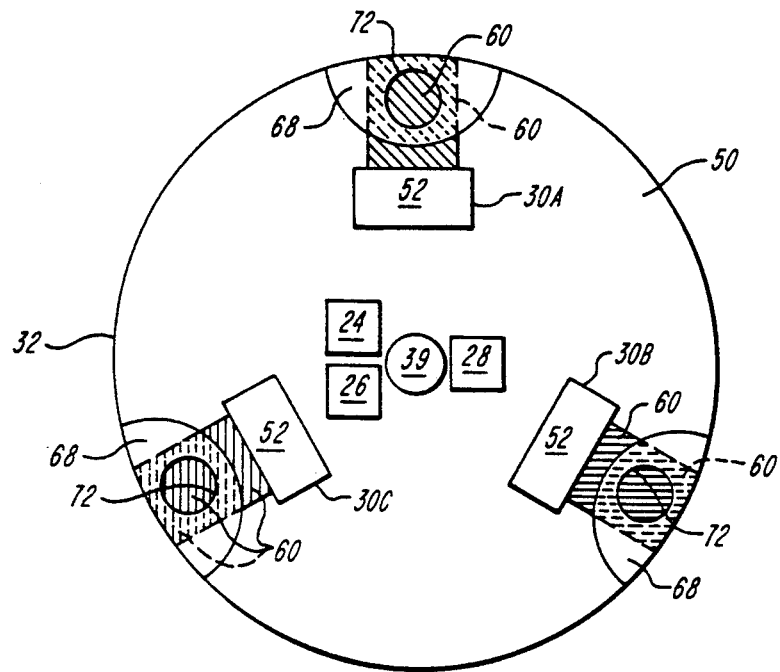
FIG. 3 is a cross-sectional top view of one sensor element of the sensor device of FIG. 2

As seen in FIG. 2, the sensor elements can be mounted on a circuit board 50, which is shown mounted in housing 22. The sensor elements are mounted relative to the surface of the circuit board according to their assigned window locations (W1-W4). As seen in FIGS. 2 and 3, elements 30A-C can be mounted at the periphery of circuit board 50, at 120° intervals, while transmitter 24, electronics package 26, battery 28, sensor element 30D, and sensors 46 and 48 also can be strategically mounted, so as to obtain a balanced device.

Figure 4:
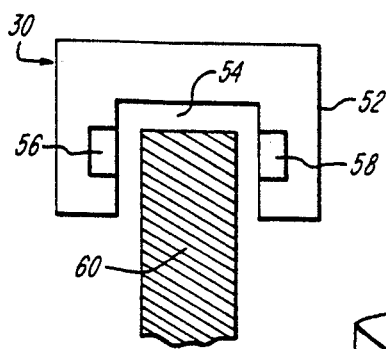
FIG. 4 is a top cross-sectional view of the sensor device of FIG. 2, taken through line 4—4 of FIG. 2.

The sensor elements 30A-D can be made according to the teachings of commonly-owned and co-pending U.S. application Ser. Nos. 07/595,037 and/or 07/796/948, both of which are incorporated herein by reference. Accordingly, as shown in FIG. 4, a sensor element 30 for sensing hydrocarbon-based fluids based on fluorescent additives in such hydrocarbons includes a housing 52 which defines a sample chamber 54, irradiation means 56 for irradiating a fluid sample drawn into the sample chamber from the ambient environment, and detection means 58 for detecting fluorescence exhibited by the irradiated sample. Most preferably, the sensor element further comprises a hydrophobic absorption means, such as a porous PTFE wick 60, disposed within the sample chamber and extending out to the periphery 32 of the housing so as to come in contact with the fluid medium 16. This absorption means draws a fluorescent hydrocarbon fluid sample from the fluid medium and into the sample chamber, wherein the irradiation means irradiates the sample and the detection means detects the level of fluorescence according to presence of hydrocarbons in the sample. The conditioning electronics of package 26 processes these signals, eliminating background noise, and issues an output accordingly.

In one embodiment, the sensor elements are binary, i.e., they indicate either the absence or presence of hydrocarbon fluid. In another embodiment, the sensor elements are tri-state, for discriminating between the absence or presence of hydrocarbon fluid, and then also for discriminating between conventionally fluorescing hydrocarbon fluids and hydrocarbon fluids doped with highly fluorescing dyes (such as coumarin) for tracing the source of leakage from tanks doped with such highly fluorescing dyes.

Returning to FIGS. 2 and 3, it will be seen that housing 22 can have a series of internal projections 68 extending radially inwardly from the housing periphery 32, with various ones of the projections being assigned to various ones of the sensor elements. For ease of presentation, the projection assigned to sensor element 30B is also assigned to sensor element 30D.

Figure 5:
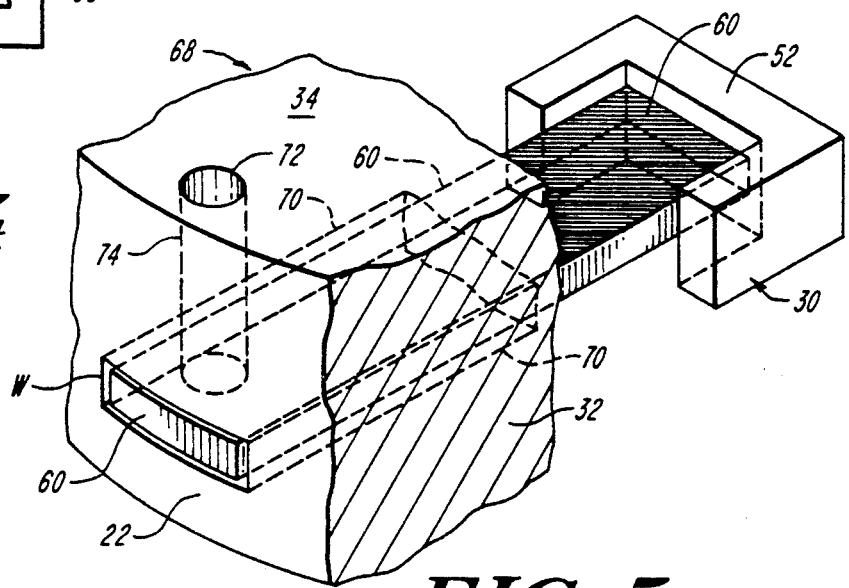
FIG. 5 is a side view of a portion of the sensor device of FIG. 4.

As shown in FIG. 5, a typical one of the projections 68 has a respective transverse slot 70 for each assigned sensor element, each slot extending from its assigned window W (e.g., windows W1-W4) at the housing periphery 32 back to the assigned sensor element 30 (e.g., sensor elements 30A-D). The slot receives wick 60 of the assigned sensor element, enabling the wick to extend from its assigned window at the housing periphery and in contact with the fluid medium into the sensor element's sample chamber 54.

Each such projection further includes a vent 72 at the top 34 of sensor device 10. The vent extends as a shaft 74 parallel to the floatation axis X down to the respective slot 70. Thus the wick 60 is vented to the ambient environment 76, which will enable the wick to self-purge its absorbed hydrocarbon sample when the level of the fluid medium 16 changes (e.g., when a thin layer of hydrocarbon fluid on the surface of the groundwater rises above the assigned window for that wick and sensor element).

The foregoing disclosure describes a sensor system 80 which provides accurate hydrocarbon contamination information regarding remote and possibly otherwise inaccessible locations. When the sensor device 10 must be serviced (such as when the battery of the sensor is replaced or the sensor is moved to a new bore hole) or when the fluid medium rises or falls and removes the hydrocarbon fluid from the level of the sensor element, then the above described venting permits the hydrocarbon fluid previously absorbed by the wick(s) to be purged therefrom, thus avoiding false hydrocarbon readings.

Housing 22 may be formed out of top and bottom portions 22A and 22B which are mated by means of threads 82 located on cooperating surfaces of the housing top and bottom portions. The device is sealed from the fluid environment by means of an o-ring 84. This sealed, threaded engagement forms a buoyancy adjustment device 86, whereby the location of the draft line 38 can be adjusted upwardly or downwardly relative to the location of the sensor elements.

In the example set forth above, sensor elements 30A-C monitor a ¼" range measured from the surface of the fluid medium when the sensor device is afloat, with optional sensor element 30D adding an addition ⅛" capacity. Of course additional sensor elements may be added, but this increases device complexity and adds to its cost. The sensor device nevertheless is useful in conditions where even a substantial hydrocarbon layer is detected beyond the range (e.g., ¼"or ⅜") of the sensor device.

Specifically, where perhaps one or more inches of hydrocarbon fluid is detected floating on top of groundwater (wherein all of the sensor elements would continuously detect hydrocarbon fluid and would not be able to signal further increases or marginal decreases in the hydrocarbon layer), the draft of the sensor device can be adjusted by means of buoyancy adjustment device 86. In this manner, at least one of the sensor elements, such as sensor element 30A, can be returned to the groundwater level. Thus, as the site is monitored, an increase in hydrocarbon fluid will be detected by sensor element 30A or a decrease will be detect by the clearing of sensor element 30B.

The bottom of the housing can be contoured slightly rounded at its bottom edges 87 and made from a material such as a solid PTFE or nylon, for example, so that if the groundwater 15 freezes, the sensor device will rise up over the formed ice and will not be captured and trapped within the ice.

It will therefore be appreciated that the present invention comprises method and apparatus for detecting and/or monitoring the presence of hydrocarbons in a fluid medium at a remote location, by sensing the presence of hydrocarbon-based fluid in the fluid medium in the remote location, generating a signal indicative of the sensed fluid, and transmitting the signal to monitoring means for indication of hydrocarbon contamination. Nevertheless, the above description pertains to only several embodiments of the present invention. That is, the description is provided by way of illustration and not by way of limitation. The invention, therefore, is to be limited according to the following claims.

What is claimed is:

1. A system for monitoring for the presence of hydrocarbon-based fluid in a remote location, the system comprising a a sensor device, said sensor device having means for sensing the presence of hydrocarbon-based fluid at at least two different vertical levels in a fluid mass in a remote location, and for generating a sense signal indicative of said sensed fluid at said different levels, said means comprising at least one sensor element at each of said two different levels, wireless communication means for wirelessly communicating said sense signal to a monitoring station for monitoring of the presence of hydrocarbon-based fluid at said different levels within said remote location, and housing means for commonly housing of said device and said communication means in said remote location.

2. The system of claim 1 wherein said communication means comprises a wireless transmitter, conditioning electronics, and a power source.

3. The system of claim 2 wherein said power source comprises a timing circuit for reduction of power consumption.

4. The system of claim 3 wherein said power source comprises a rechargeable battery.

5. The system of claim 1 wherein said housing means extends along a floatation axis and said sensor elements are located of different axial locations along said axis for sensing said different levels relative to the surface of said fluid mass.

6. The system of claim 1 wherein said sensor device is a floating device.

7. The system of claim 6 wherein said housing means comprises a buoyancy adjustment means for adjusting the buoyancy of said floating sensor device.

8. The system of claim 6 further comprising means for detecting when the sensor device is not floating.

9. The system of claim 6 wherein said housing has a bottom comprising an ice rejection means for lifting said sensor device out of ice forming at said bottom.

10. The system of claim 9 wherein said ice rejection means comprises a material layer on said housing bottom.

11. The system of claim 1 wherein said means for sensing is for sensing hydrocarbon-based fluids based on detection of fluorescent components of said fluids.

12. The system of claim 11 wherein said means for sensing comprises a housing defining a sample chamber, irradiation means for irradiating a fluid sample drawn into the sample chamber from said fluid, and detection means for detecting fluorescence exhibited by the irradiated sample.

13. The system of claim 12 wherein said means for sensing further comprises a hydrophobic absorption means for communication between said sample chamber and said fluid.

14. The system of claim 13 wherein said absorption means comprises a porous wick.

15. The system of claim 14 wherein said sensor device is a device for floating at the surface of said fluid, and said sensor device further comprises a housing having vents opening out above said fluid surface when said sensor device is floating at said fluid surface, and wherein said wicks are vented by said vents above said fluid surface.

16. The system of claim 1 wherein said communication means further comprises a wireless transmitter for transmission of said sense signal, said system further comprising a cooperating receiver means, said receiver means for wireless receipt of said transmitted sense signal and for communication of said received transmitted sense signal to said monitoring station.

17. The system of claim 16 wherein said remote location is a bore hole and said receiver further comprises housing means for location of said receiver adjacent to said sensor device in said bore hole.

18. The system of claim 16 wherein said system further comprises means for detecting a layer of hydrocarbon-based fuel accumulated in an overflow pan for a hydrocarbon-based fuel pump.

19. The system of claim 16 wherein said system further comprises means for detecting a layer of hydrocarbon-based fuel accumulated in an interstitial chamber within a double walled tank.

20. The system of claim 16 wherein said system further comprises means for detecting a layer of hydrocarbon-based fuel accumulated in a sump.

21. The system of claim 1 wherein said sensor device extends along a floatation axis and further comprises guidance means for guiding said sensor device along said axis as said sensor device floats on said fluid.

22. The system of claim 21 further comprising sensor means for detecting when said sensor device is not floating.

23. A system for monitoring for the presence of hydrocarbon-based fluid in a fluid medium in a remote location, the system comprising a sensor device for monitoring a fluid medium, said sensor device including a buoyant housing, said housing having a calibration index, and means mounted in said housing for sensing the presence of hydrocarbon-based fluid in a remote location and for generating a sense signal indicative of said sensed fluid, said means including a plurality of fluid level sensor elements mounted at different respective axial locations relative to said housing for sensing a plurality of depths of said fluid relative to said calibration index.

24. The system of claim 23 wherein said calibration index is a draft line at which said sensor device is afloat in said fluid, and said plurality of fluid level sensor elements are mounted at respective distances from said draft line.

25. The system of claim 24 wherein said sensor device has a buoyancy adjustment means for changing the location of said draft line relative to said plurality of fluid level sensor elements.

26. A method for monitoring for the presence of hydrocarbon-based fluid in a fluid medium in a remote location, comprising the steps of providing a housed sensing device, including at least two sensor elements, for sensing the presence of hydrocarbon-based fluid in a remote location at at least two different vertical levels in a fluid mass by using at least one of said sensor element at each of said two different levels, generating a sense signal indicative of said sensed fluid at said different levels, and wirelessly transmitting said sense signal to monitoring means for monitoring the presence of said hydrocarbon-based fluid at said different levels within said remote location.

27. A method for monitoring for the presence of hydrocarbon-based fluid in a fluid medium in a remote location, comprising the steps of monitoring a fluid medium in a remote location with a sensor device having a buoyant housing, said housing having a calibration index, and sensing, with a plurality of axially separated fluid level sensor elements mounted on said housing, the presence of hydrocarbon-based fluid in said fluid medium, and generating a sense signal indicative of said sensed hydrocarbon-based fluid, for monitoring the presence of said hydrocarbon-based fluid at a plurality of depths in said fluid medium relative to said calibration index.

28. The method of claim 27 wherein said calibration index is a draft line at which said sensor device is afloat in said fluid, and said plurality of fluid level sensor elements are mounted at respective distances from said draft line.

* * * * *